United States Patent
Petroff (12) 
(10) Patent No.: US 8,206,377 B2
(45) Date of Patent: Jun. 26, 2012

(54) TORQUE LIMITER FOR AN OCT CATHETER

(75) Inventor: Christopher Petroff, Groton, MA (US)

(73) Assignee: LightLab Imaging, Inc., Westford, MA (US)

( * ) Notice: Subject to any disclaimer, the term of this patent is extended or adjusted under 35 U.S.C. 154(b) by 290 days.

(21) Appl. No.: 12/645,032

(22) Filed: Dec. 22, 2009

(65) Prior Publication Data

US 2011/0151980 A1 Jun. 23, 2011

(51) Int. Cl.
*A61M 39/12* (2006.01)
(52) U.S. Cl. .......................................... 604/535; 464/32
(58) Field of Classification Search ............... 464/32; 604/533–535; 600/136; 356/477; 403/2
See application file for complete search history.

(56) References Cited

U.S. PATENT DOCUMENTS

| | | | |
|---|---|---|---|
| 3,306,291 A | 2/1967 | Burke | |
| 4,434,904 A | 3/1984 | D'Amico et al. | |
| 4,669,999 A | 6/1987 | Miller | |
| 4,971,267 A * | 11/1990 | Fulton et al. | 464/32 X |
| 5,185,004 A * | 2/1993 | Lashinski | 604/533 X |
| 5,228,441 A | 7/1993 | Lundquist | |
| 5,321,501 A | 6/1994 | Swanson et al. | |
| 5,368,480 A | 11/1994 | Balfour et al. | |
| 5,459,570 A | 10/1995 | Swanson et al. | |
| 5,465,147 A | 11/1995 | Swanson | |
| 5,509,093 A | 4/1996 | Miller et al. | |
| 5,596,996 A | 1/1997 | Johanson et al. | |
| 5,619,368 A | 4/1997 | Swanson | |
| 5,748,598 A | 5/1998 | Swanson et al. | |
| 5,784,352 A | 7/1998 | Swanson et al. | |
| 5,913,437 A | 6/1999 | Ma | |
| 5,956,355 A | 9/1999 | Swanson et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |

(Continued)

FOREIGN PATENT DOCUMENTS

EP 0445918 9/1991

(Continued)

OTHER PUBLICATIONS

Mondofacto, Charriere Scale, [online] Mar. 5, 2000 [retrieved Feb. 1, 2012]. Retrieved from the Internet URL: http://www.mondofacto.com/facts/dictionary?Charriere+scale.*

(Continued)

*Primary Examiner* — Gregory Binda
(74) *Attorney, Agent, or Firm* — K&L Gates LLP (57) ABSTRACT

An apparatus comprising a torque wire connected to an imaging probe; and a torque limiter defining a bore, a first end of the torque limiter being in mechanical communication with a motor, a second end of the torque limiter being in mechanical communication with the torque wire, the torque wire being disposed through the bore of the torque limiter. The torque limiter comprises a member defining at least one cutout which causes the torque limiter to break when rotational force on the torque wire exceeds a predetermined amount, thereby decoupling the motor from the torque wire.

20 Claims, 8 Drawing Sheets

U.S. PATENT DOCUMENTS

| | | | |
|---|---|---|---|
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,582,368 B2 | 6/2003 | Holdaway et al. |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,066,819 B2 | 6/2006 | Ueda et al. |
| 7,121,947 B2 | 10/2006 | Ueda et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,311,625 B2 | 12/2007 | Nosaka et al. |
| 7,407,440 B2 | 8/2008 | White |
| 7,414,779 B2 | 8/2008 | Huber et al. |
| 7,415,049 B2 | 8/2008 | Flanders et al. |
| 7,625,366 B2 | 12/2009 | Atlas |
| 7,813,609 B2 | 10/2010 | Petersen et al. |
| 7,848,791 B2 | 12/2010 | Schmitt et al. |
| 7,916,387 B2 | 3/2011 | Schmitt |
| 7,935,060 B2 | 5/2011 | Schmitt et al. |
| 2002/0151799 A1 | 10/2002 | Pantages et al. |
| 2002/0161351 A1 | 10/2002 | Samson et al. |
| 2004/0186368 A1 | 9/2004 | Ramzipoor et al. |
| 2004/0215166 A1 | 10/2004 | Atlas |
| 2005/0201662 A1 | 9/2005 | Petersen et al. |
| 2006/0095065 A1 | 5/2006 | Tanimura et al. |
| 2006/0241503 A1 | 10/2006 | Schmitt et al. |
| 2007/0232892 A1 | 10/2007 | Hirota |
| 2007/0232893 A1 | 10/2007 | Tanioka |
| 2007/0260198 A1 | 11/2007 | Atlas |
| 2007/0260227 A1 | 11/2007 | Phan |
| 2008/0161696 A1 | 7/2008 | Schmitt et al. |
| 2008/0165366 A1 | 7/2008 | Schmitt et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |

FOREIGN PATENT DOCUMENTS

| | | |
|---|---|---|
| JP | 07-184888 | 7/1995 |
| JP | 10-66696 | 3/1998 |
| WO | 2007139457 | 12/2007 |
| WO | 2008121234 | 10/2008 |

OTHER PUBLICATIONS

PCT International Search Report for International Patent Application No. PCT/US2010/061613, mailed Feb. 22, 2011, 3 pages.

PCT Written Opinion of International Searching Authority for International Patent Application No. PCT/US2010/061613, mailed Feb. 22, 2011, 6 pages.

\* cited by examiner

TORQUE LIMITER FOR AN OCT CATHETER

TECHNICAL FIELD

Provided are devices and methods for limiting the rotational force imparted on an imaging probe spinning inside a patient to reduce the likelihood of an unsafe condition should the imaging probe suddenly bind.

BACKGROUND

Imaging of body lumens (e.g., vasculature) can require relatively high torque and relatively high rotational speeds to spin an imaging probe, such as an optical coherence tomography (OCT) probe, inside the body lumen. Generally, an OCT imaging probe is inserted in a body lumen of a patient and a motor located outside the patient spins a torque wire which is connected to the OCT imaging probe. OCT imaging systems have unique torque wire requirements as the optical fiber rotates inside of the torque wire, adding mass and stiffness. However, high torque and high speed rotation can pose a significant risk of patient harm should the OCT probe unexpectedly bind because the motor will continue spinning the torque wire, causing the torque wire to twist on itself and spin the catheter sheath which encloses the torque wire inside the body lumen, potentially causing patient harm.

SUMMARY OF THE INVENTION

In one aspect, the invention relates to an apparatus including a torque wire connected to an imaging probe; and a torque limiter defining a bore, a first end of the torque limiter being in mechanical communication with a motor, a second end of the torque limiter being in mechanical communication with the torque wire, the optical fiber being disposed through the bore of the torque limiter. The torque limiter includes a member defining at least one cutout which causes the torque limiter to break when rotational force on the torque wire exceeds a predetermined amount, thereby decoupling the motor from the torque wire.

In another aspect, the invention provides an apparatus including: (a) a torque wire connected to an optical coherence tomography imaging probe; and (b) a torque limiter defining a bore, a first end of the torque limiter being in mechanical communication with a motor, a second end of the torque limiter being in mechanical communication with the torque wire, the torque wire being disposed through the bore of the torque limiter, the torque limiter comprising a member defining at least one cutout which causes the torque limiter to break when rotational force on the torque wire exceeds a predetermined amount, thereby decoupling the motor from the torque wire.

In another aspect, the invention provides an apparatus including: (a) a first member defining a bore; (b) a second member defining a bore, the first member and the second member being adjacent to one another, the bore of the first member being in concentric alignment with the bore of the second member; (c) a torque wire disposed in the bore of the first member and in the bore of the second member; and (d) a third member defining a bore, the second member and a least a portion of the first member being disposed in the bore of the third member, the third member being attached to the first member at a first attachment point of the third member, the third member being attached to the torque wire at a second attachment point of the third member, the second member disposed between the first attachment point and the second attachment point, the third member comprising at least one cutout between the first attachment point and the second attachment point. Thus, rotational force which is imparted on the first member is transferred to the torque wire, and the third member breaks and decouples the first member from the torque wire when the rotational force on the torque wire exceeds a predetermined amount.

In another aspect, the invention provides an apparatus including: (a) a first member defining an axial bore; (b) a second member defining an axial bore in concentric alignment with the axial bore of the first member, the second member comprising a proximal end defining a first outer diameter and a distal end defining a second outer diameter, the second outer diameter being larger than the first outer diameter, the axial bore of the first member configured to concentrically receive the proximal end of the second member; (c) a torque wire disposed in the axial bore of the first member and the axial bore of second member; and (d) a third member defining an axial bore which concentrically receives at least a portion of the first member and the second member, the third member being attached to the first member at a first attachment point of the third member, the third member being attached to the torque wire at a second attachment point of the third member, the second member disposed between the first attachment point and the second attachment point, the third member comprising at least one cutout between the first attachment point and the second attachment point. Thus, rotational force which is imparted on the first member is transferred to the torque wire, and the third member breaks and decouples the first member from the torque wire when the rotational force on the torque wire exceeds a predetermined amount.

Embodiments of the apparatus can include one or more of the following features.

In some embodiments, the first member comprises metal, such as, for example, Nitinol.

In some embodiments, the second member reduces flexure between the first attachment point and the second attachment point.

In some embodiments, the third member comprises poly (ethylene terephthalate), and in some embodiments the poly (ethylene terephthalate) has a fracture strength of about 0.05 oz-in.

In some embodiments, the third member comprises two or more cutouts.

In some embodiments, the torque wire defines an axial bore and the apparatus comprises an optical fiber disposed in the bore.

In some embodiments, the optical fiber comprises glass fiber, and in some embodiments, the optical fiber stretches in the axial direction less than about 0.005 inches.

BRIEF DESCRIPTION OF THE DRAWINGS

The objects and features of the invention can be better understood with reference to the drawings described below. The drawings are not necessarily to drawn to scale; emphasis is placed instead being placed on illustrating the principles of the invention. In the drawings, numerals are used to indicate specific parts throughout the various views. The drawings associated with the disclosure are addressed on an individual basis within the disclosure as they are introduced.

DETAILED DESCRIPTION

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

The use of headings and sections in the application is not meant to limit the invention; each section can apply to any aspect, embodiment, or feature of the invention.

The order of steps in the methods described herein is immaterial so long as the invention remains operable. Moreover, two or more steps may be conducted simultaneously or in a different order than recited herein unless otherwise specified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value, unless otherwise indicated or inferred.

It should be understood that the order of steps or order for performing certain actions is immaterial so long as the present teachings remain operable. Moreover, two or more steps or actions may be conducted simultaneously. The invention provides, in part, OCT imaging systems that incorporate a torque limiter which reduces the chance of patient injury should the OCT imaging probe unexpectedly bind. In some embodiments, this is accomplished by using a torque limiter to couple the torque wire to a drive member, such as a tube, which is in communication with the motor. Specifically, the torque limiter is configured to deliberately break or fail when the system experiences torsional forces above a predetermined amount or threshold. Upon breakage or failure of the torque limiter, the motor becomes disconnected from the torque wire, allowing the torque wire and imaging probe to slow down or stop independent of the rotational speed of the motor.

In some embodiments, the imaging probe is carried in a delivery catheter. Once at the imaging site, the rotating imaging probe is then pulled back rapidly towards the body entry point. As a result, the imaging core is therefore subject to axial and torsional stresses during pullback.

Thus, the invention also provides, in part, an OCT imaging system which separates torsional and tensile forces, thereby permitting optimum functionality and relatively inexpensive manufacturing. In some embodiments, the torsional forces required to spin the imaging probe are transmitted primarily via the torque limiter and/or the torque wire, while the tensile forces required to withdraw or pull back the probe are transmitted primarily by an optical fiber disposed in the torque wire. These embodiments are beneficial because the torque limiter and torque wire can be designed for optimal torsional strength at the expense of having significant tensile strength. It also allows the torque limiter of the break away section to be relatively inexpensive to manufacture. In some embodiments, the optical fiber can have optimal tensile strength at the expense of having significant torsional strength; this further reduces manufacturing cost and improves the reliability of the torque limiter. For example, in some embodiments the optical fiber is configured to stretch in the axial direction less than about 0.005 inches and, more preferably, less than about 0.001 inches.

Figure 1A:
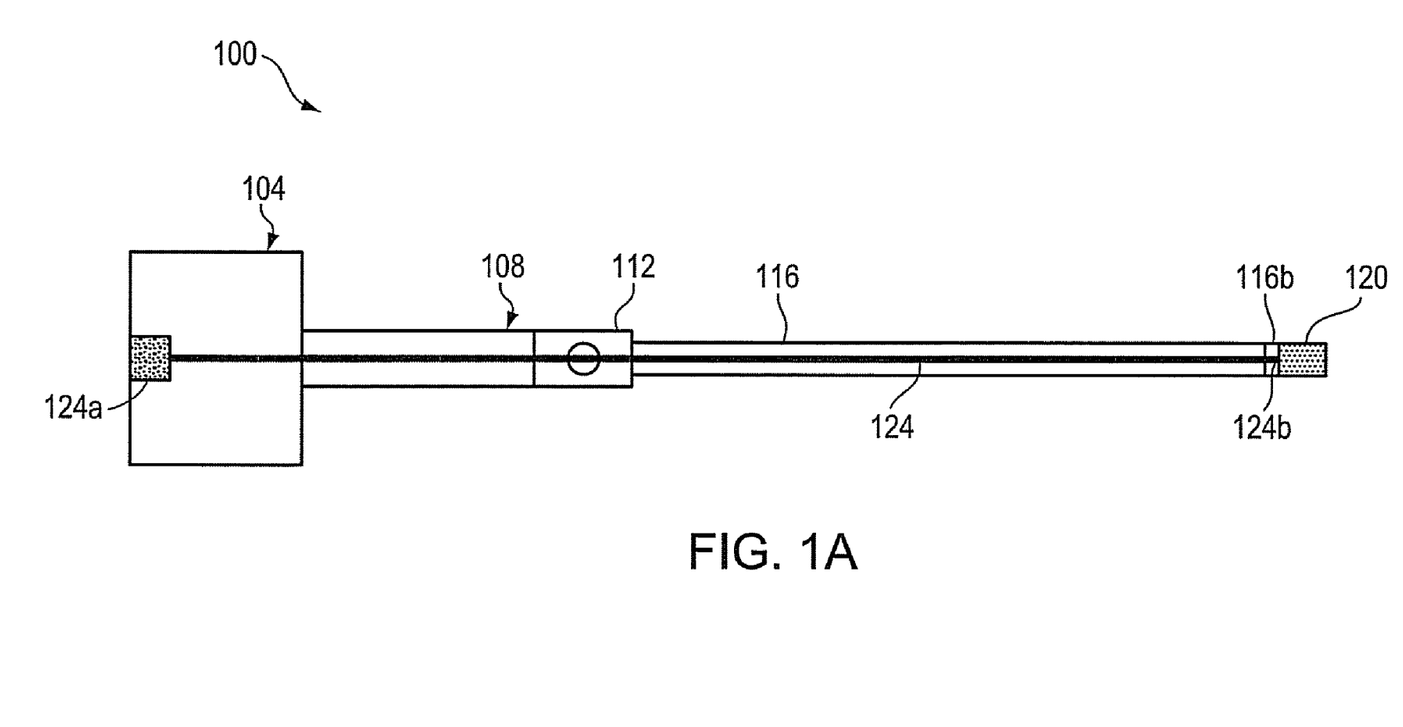
FIG. 1A is schematic diagrams showing an OCT rotating imaging core, in accordance with an illustrative embodiment.

An OCT system generally comprises an imaging core that is mechanically coupled to a motor which spins one or more components of the imaging core. FIG. 1A shows a schematic diagram of a rotating imaging core 100, in accordance with an illustrative embodiment. Rotating imaging core 100 includes, from proximal to distal, an optical connector 104 which turns a tube 108 which, via a torque limiter 112, turns torque wire 116. An optical probe 120 connected to the distal end 116b of torque wire 116 turns as the distal end of the torque wire turns. An optical fiber 124 connects at its proximal end 124a to optical connector 104 and at its distal end 124b to optical probe 120. Optical fiber 124 can be carried inside torque wire 116 along all or a portion of the optical fiber's length. In some embodiments, the torque wire 116 extends from the imaging probe 120 to the break away section, though the torque wire 116 can extend as far as the optical connector 104. The torque wire 116 can be disposed in a delivery catheter to facilitate insertion of the torque wire 116 and probe 120 into a body lumen.

Figure 1B:
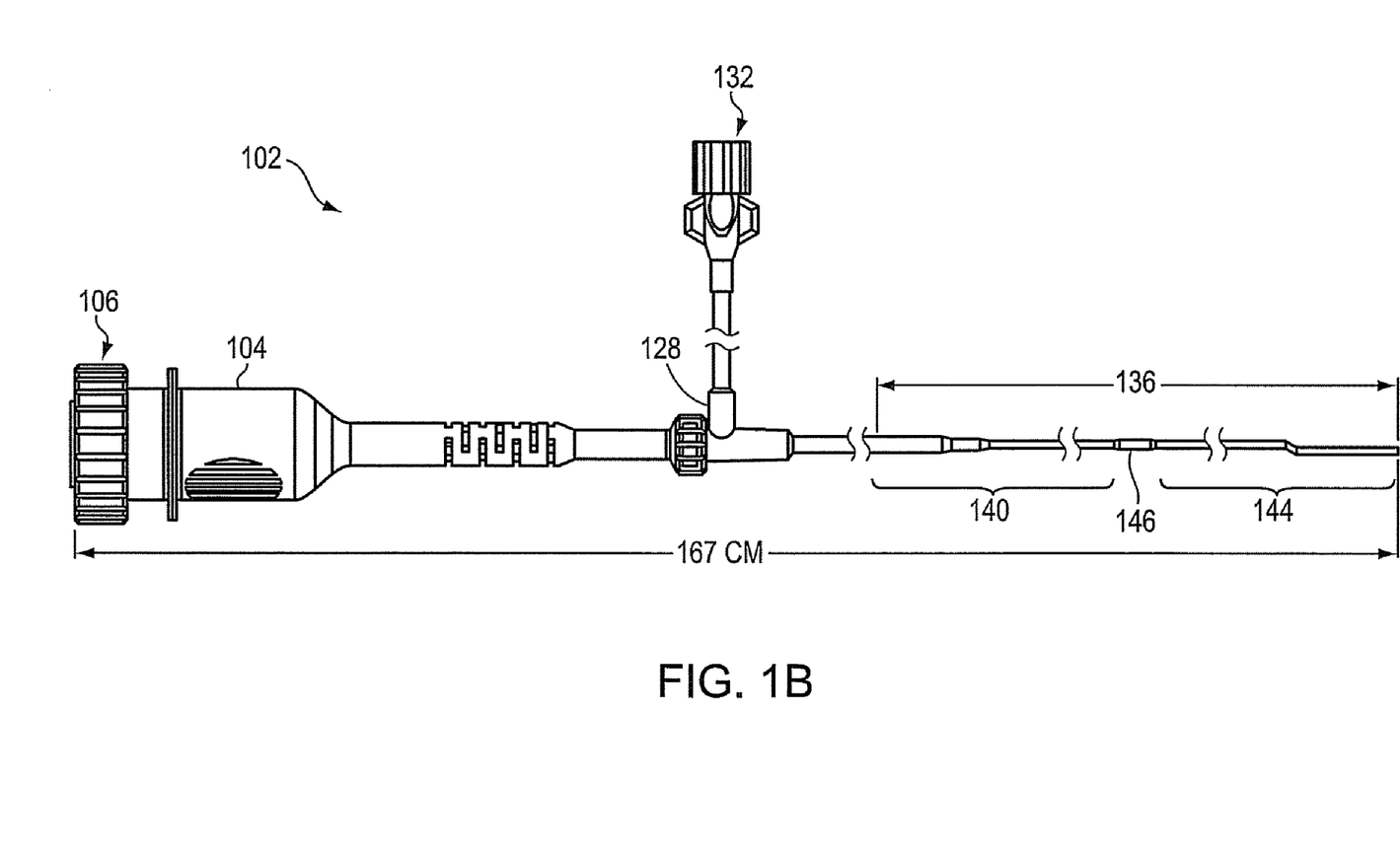
FIG. 1B is a schematic diagram of an OCT catheter constructed in accordance with the invention.

FIG. 1B shows a rotating imaging OCT catheter 102 including its housing, in accordance with an illustrative embodiment. The imaging OCT catheter 102 can be, for example, about 167 cm in length. In one embodiment, the entire catheter 102 is disposable. The housing of optical connector 104 is configured to easily connect 106 to OCT hardware which spins the imaging core and which receives and processes imaging data. In the embodiment shown in FIG. 1B, the rotating imaging core includes a side port 128 for accepting a fluid, such as a purge fluid. The side port 128 can include a luer connector 132 or other connector which facilitates connection to peripheral devices, such as a syringe.

With further reference to FIG. 1B, the imaging core system 102 includes a portion which is inserted into the patient 136. The insertable portion 136 can be, for example, about 135 cm in length, and can have multiple sections. In some embodiments, a first section 140 proximal to the optical connector 104 can be rigid to aid in pushing the optical fiber through a body lumen to an imaging location while a second section 144 distal to the optical connector can be flexible to accommodate the geometry of the imaging location. The first section 140 and second section 144 are connected at a joint 146, which in some embodiments has a diameter of about 3.4 French or less. In some embodiments, the torque limiter section is position in the proximal end of the first section 140, where the diameter is large. However, it will be appreciated that the torque limiter can be positioned in many suitable locations.

Figure 2A:
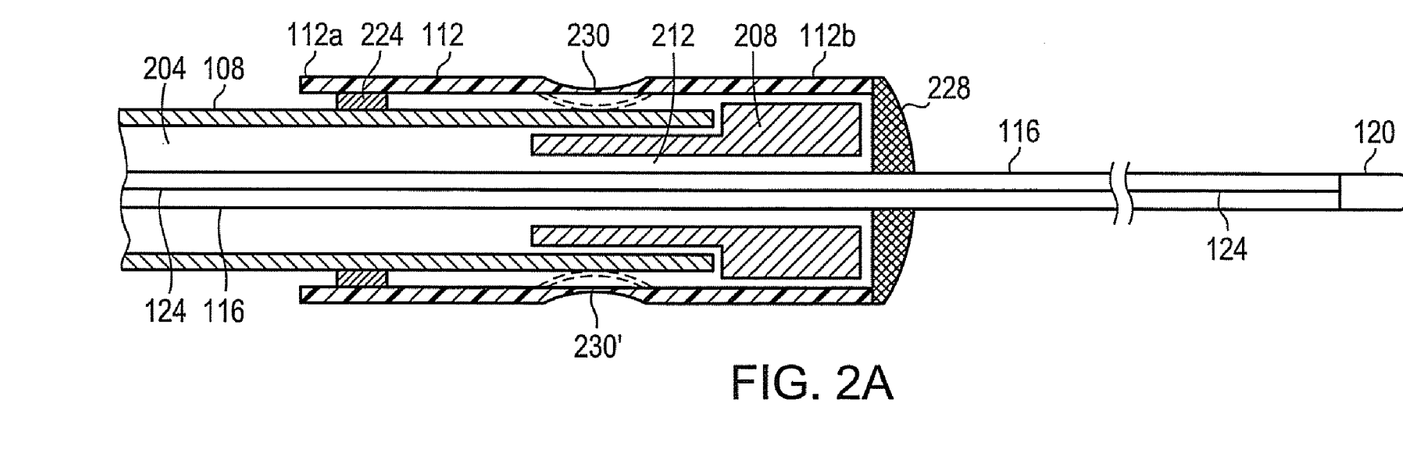
FIGS. 2A to 2D are schematic diagrams showing a longitudinal cross-section of a break away section, including a torque limiter, in accordance with an illustrative embodiment.

Referring to FIG. 2A, in some embodiments, the torque limiter section of the rotating imaging core receives a tube 108 defining a bore 204. Tube 108 can be made of any suitable material such as metal and, for example, a shape memory metal. In a preferred embodiment, tube 108 is made of Nitinol. Through the tube bore 204 is positioned a torque wire 116 through which is positioned an optical fiber 124. Within the distal end of the tube 108 is located a portion of a spacer 208. In the embodiment shown in FIG. 2A, the spacer 208 has a first, proximal portion with a smaller diameter than a second, distal portion which has a larger diameter. The first portion of the spacer is sized and configured to concentrically receive the distal end of the tube 108. The spacer 208 also defines a bore 212 through which passes the torque wire 116 and optical fiber 124. The bore of the tube 108 and the spacer are concentric in some embodiments. The spacer can be made of any suitable material such as, for example, metal or plastic. In some embodiments, the spacer is steel.

In some embodiments, the spacer 208 and tube 108 are not attached to one another. Instead, a cylindrical torque limiter 112 is positioned over the area of overlap between the tube 108 and spacer 208. The proximal end 112a of the torque limiter 112 is glued 224 to the tube 108 and the distal end of the torque limiter 112b is glued 228 to the torque wire. The inclusion of the spacer helps to prevent glue migration between the tube 108 and the torque wire 116, and also helps to stiffen the break away joint and prevent premature breakage of the torque limiter 112. Thus, as the tube 108 rotates, torque is transferred by the torque limiter 112 to the torque wire. In some embodiments, the distal end 112b of the torque limiter 112 is glued to the spacer 208 and the distal end of the spacer 208, in turn, is glued to the torque wire 116. Thus, as the tube 208 rotates, the torque wire 116 also rotates. UV glue is useful for gluing the torque limiter 112 to tube 108 and the spacer 208 because UV glue, due to its rapid cure time, can be cured with minimal migration.

Figure 2B:
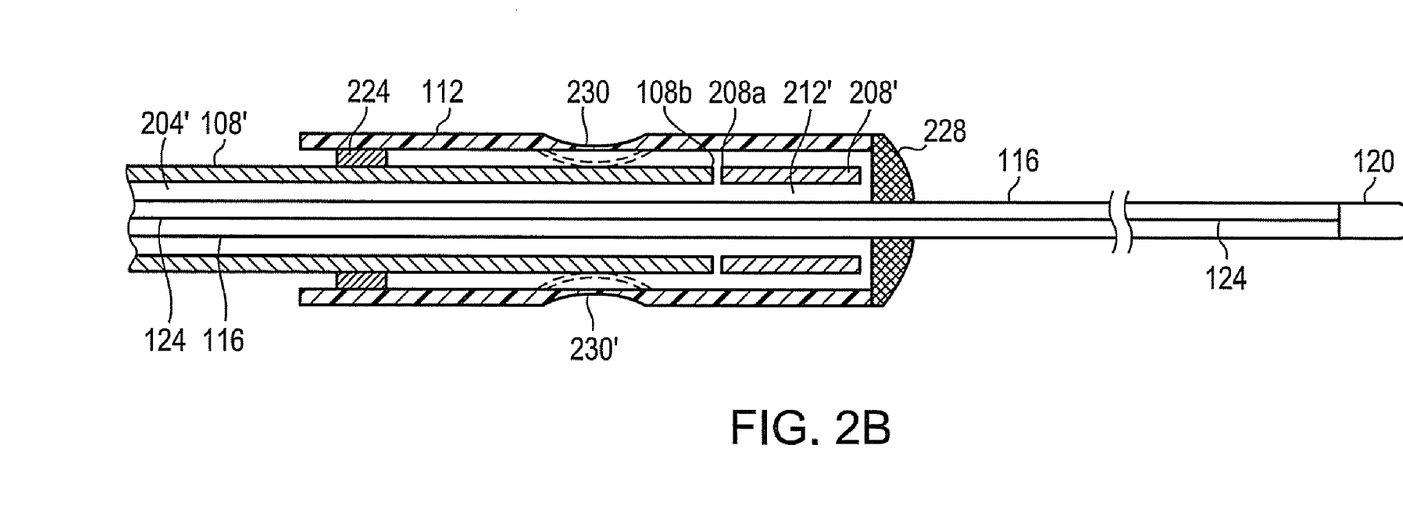

Referring to FIG. 2B, in another embodiment, a portion of the spacer 208' is not positioned within the tube 108'. This distal end 108b of the tube 108' can abut the proximal end 208a of the spacer 208'. In some embodiments, there can be a small gap between the distal end 108b of tube 108' and the proximal end 208a of spacer 208'; however, the gap cannot be so large as to cause flexure and breakage of the torque limiter 112 in use. The ends 108b and 208a are not attached to one another. The torque limiter 112 is positioned over the two ends and again each end of the torque limiter 112 is glued to tube 108' and glued 228 to the torque wire 116; or the torque limiter 112 can be glued 224 to the tube 108' and to the spacer 208', and the spacer to the torque wire 116.

Figure 2C:
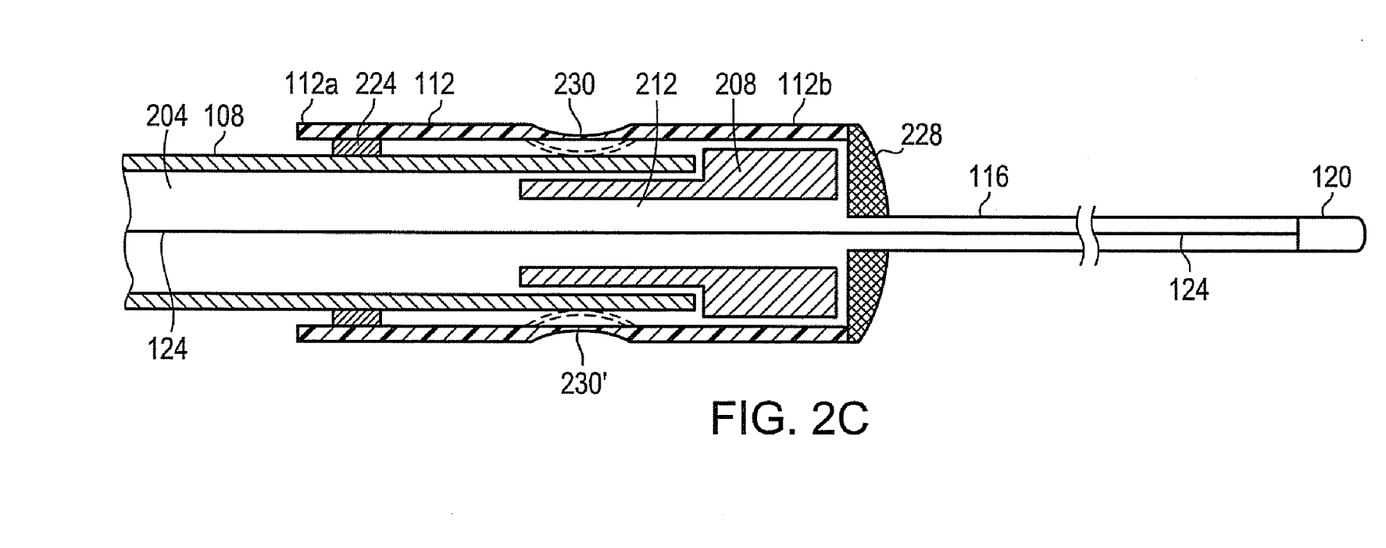
Figure 2D:
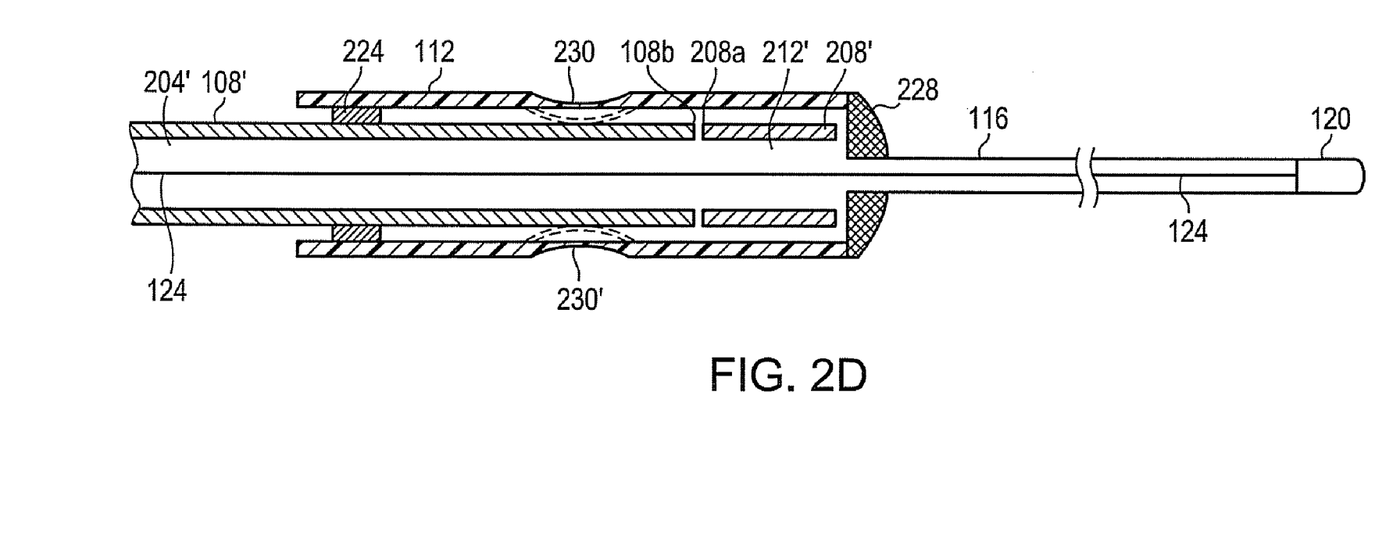

Referring to FIGS. 2C and 2D, in some embodiments the torque wire 116 extends at least from the imaging probe 120 to the torque limiter 112, where the torque wire 112 is connected to the torque limiter 112 or spacer 208 as discussed above. However, the torque wire 116 can also extend through all or a portion of the torque limiter 112 as shown in FIGS. 2A and 2B, and as far as the optical connector, if desired. It will also be appreciated that the invention is not limited to torque wires specifically, and that the torque limiter of the present invention can be used with any rotary drive mechanism suitable for use with an optical coherence tomography imaging system.

Figure 3:
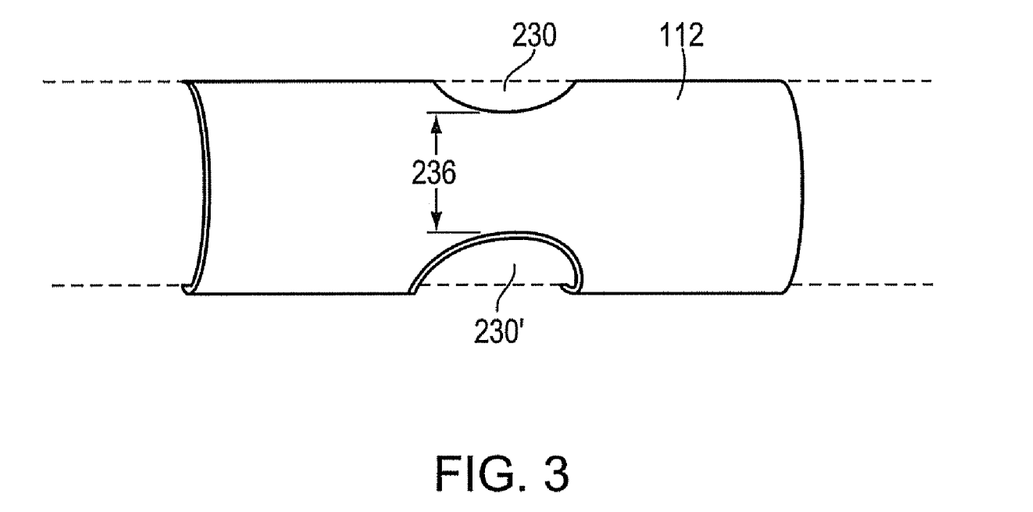
FIG. 3 is a schematic diagram showing a torque limiter, in accordance with an illustrative embodiment.

Referring to FIG. 3, the torque limiter 112 is a cylindrical tube which, in some embodiments, includes one or more "cutouts" 230, 230' or through-holes in the cylinder wall. Cutouts 230, 230' weaken the torque limiter provide a region for shear if the torque on the torque limiter 112 exceeds the shear strength of the material of the torque limiter 112 at the region of the cutouts 230, 230'.

The strength of the torque limiter 112 can be controlled by its cross-sectional area, thickness, cutout size, and/or geometry. Large cutouts or more cutouts reduce the amount of material in a given cross-section and therefore will reduce the torsional strength of the torque limiter 112. Similarly, wall thickness of the torque limiter 112 will also affect its breaking strength. In a preferred embodiment, the torque limiter 112 has an inside diameter of about 0.043±0.002 inches and a wall thickness of about 0.001 inches. In some embodiments, the torque limiter 112 has a minimum length of about 0.5 cm and can be, for example, between about 0.5 cm to about 10.0 cm in length. In a preferred embodiment, the torque limiter 112 is about 3.0 cm in length. In some embodiments, the cutouts 230, 230' are substantially circular. In a preferred embodiment, there are two substantially circular cutouts 230, 230' which are sized such that the cutouts are separated by about 350 μm of material 236. As will be appreciated, a variety of cutout shapes, number, and arrangements can be employed to similar effect.

The torque limiter 112 can be made of any suitable material which can withstand significant rotational force and yet reliably break when a threshold amount of torque is experienced. In some embodiments, the torque limiter 112 is made of plastic such as, for example, poly(ethylene terephthalate) (PET). In a preferred embodiment, the PET has fracture strength of about 0.05 oz-in.

Thus, in use, if the torque wire 116 being spun by the tube 108, binds within the channel in which it is positioned, the torque wire 116 slows or stops and causes the glued end 224 of the spacer 208 to slow or stop. However, the tube 108 continues to rotate and thereby causes the other end of the torque limiter 112 to attempt to continue to spin. This causes a strong torque within the body of the torque limiter 112. This torque causes the torque limiter 112 to experience shear at the cutouts 230, 230'. The shearing of the torque limiter 112 permits the tube 108 end of the torque limiter 112 to continue to rotate while permitting the spacer end 208 of the torque limiter 112 to stop. This prevents the transmission of torque to the torque wire 116 and prevents the bound torque wire 116 from damaging the location in the channel in which the torque wire binds or any other location in the body.

Figure 4A:
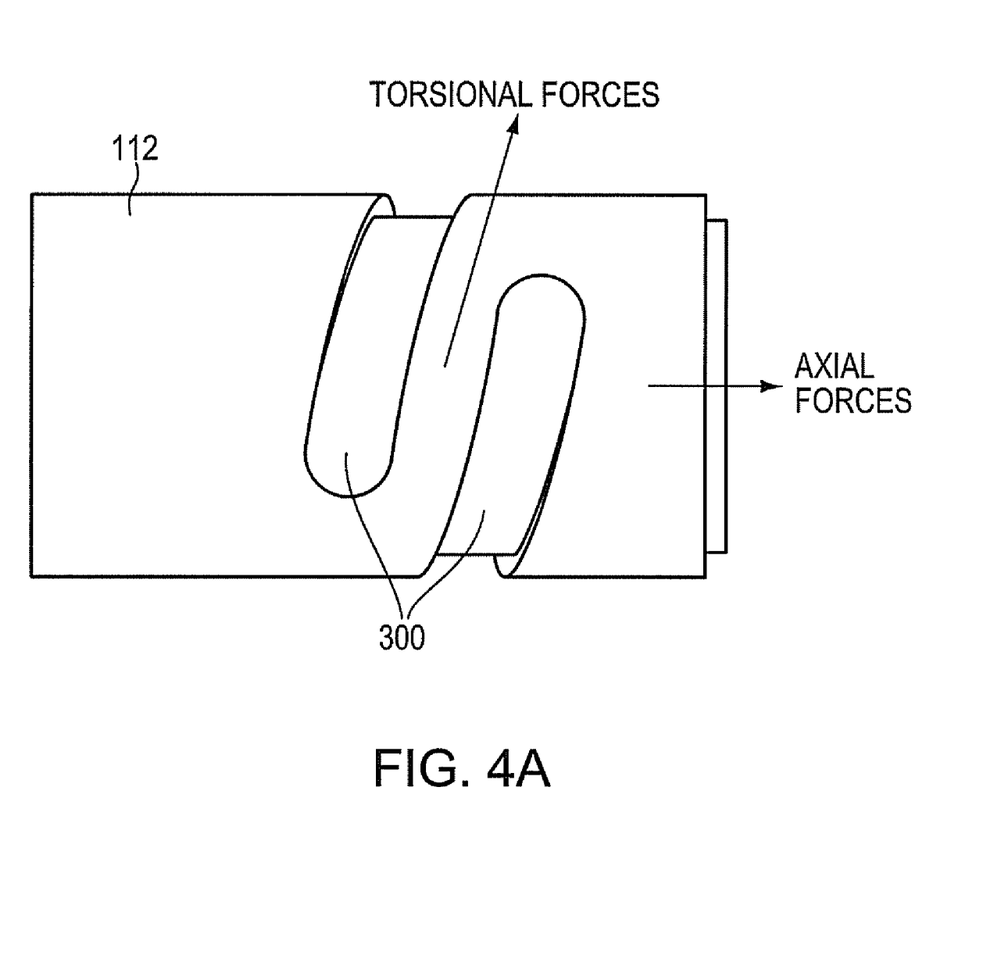
FIG. 4A is a schematic diagram and FIG. 4B is a computer model of a torque limiter, in accordance with an illustrative embodiment.
Figure 4B:
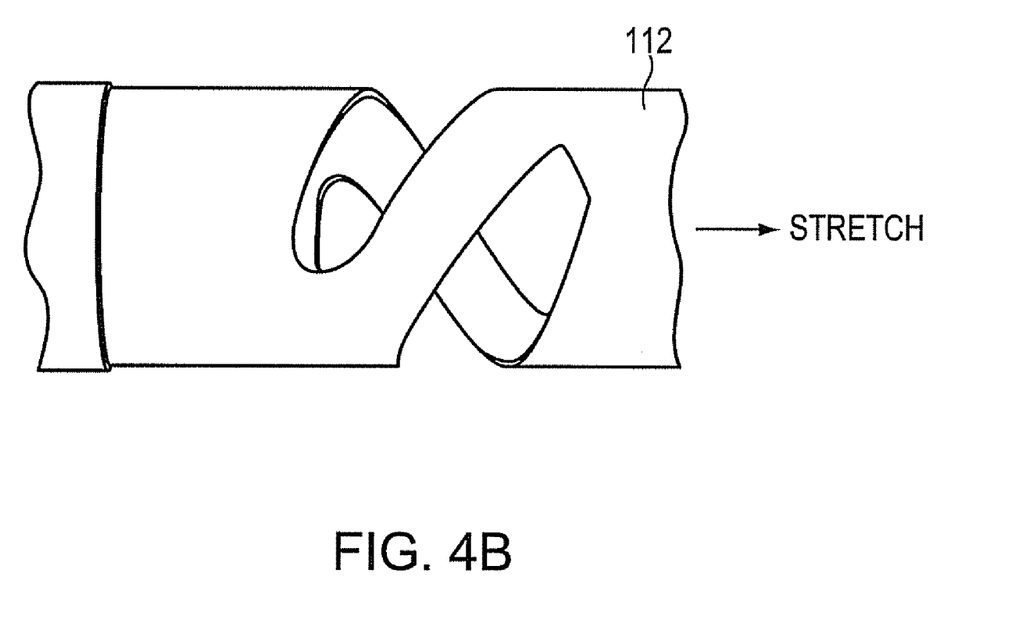

Although shown as having one or more cutouts 230, 230', the torque limiter may take on other forms. Referring to FIGS. 4A and 4B, another embodiment of the torque limiter is shown in which the two ends of the torque limiter cylinder 112 are separated by a helical-shaped cutout 300.

In some embodiments, as an additional safeguard the glue used on the torque limiter 112 is designed to fail when a threshold amount of torque is experienced. This can be accomplished by, for example, using less glue and/or low-strength glue, such as, for example, thread locker glue. Appropriate controls can be used to provide repeatable glue coverage to reduce variability.

The optical fiber passes through the torque limiter section of the imaging core and can add significant axial strength. In some embodiments, the optical fiber has a small diameter, and therefore does not provide significant additional torsional strength to the torque limiter and thus does not interfere in its break away function. The optical fiber can be made of silica glass, which has a very high tensile strength. The optical fiber also transmits imaging data from the imaging probe to the optical connector. Data transmission is not compromised by the axial stresses of normal operation.

As will be appreciated, if an optical fiber is not present in the imaging core, a different tensile member may be used that possesses high axial strength but low torsional strength, such as glass and carbon fiber. Preferably, the material is brittle to cause it to break in torsion rather than wind up on itself.

Referring again to FIG. 1A, the optical fiber 124 is attached to the image core 100 proximally at the optical connector 124a and distally at the imaging probe 120. The amount the torque limiter 112 will axially stretch due to axial friction on the probe 120 during pullback is:

$$S = F * L * A / E$$

Where:
S: Stretch on the torque limiter
F: Axial friction from image core pullback
L: Length between the attachments points 124a and 124b
A: Cross sectional area of the fiber
E: Modulus of Elasticity of the glass in the fiber.

Ideally, for a given axial friction force F, the stretch, S, on the torque limiter section is as small as possible because excess stretch can compromise the integrity of the torque limiter. Generally, A and E are set by optical requirements and other mechanical requirements, although there is some flexibility on the optical fiber diameter, which affects A. Thus, the distance between the optical fiber attachment points, L, is a variable that can be controlled to change the stretch on the torque limiter. Accordingly, in some embodiments, additional intermediate fiber attachment points may be incorporated in the design to reduce the stretch, S, on the fiber. For example, intermediate attachment points may be added just distal and proximal to the torque limiter to minimize S. While this would provide the minimum stretch for a given axial force, it has a disadvantage in that the fiber will take up a significant torsional load before the torque limiter joint fails.

With the disclosed PET material, the torque limiter will fail when twisted through about 15°. In addition, the fiber's contribution to torque is given by:

$$T = Theta * J * G / L$$

Where:
T: The optical fiber's contribution to torsional strength
Theta: Amount of twist of the fiber at the torque limiter's failure point (About 15°)
L: Length between the attachments points 124a and 124b
J: Polar moment of inertia of the optical fiber
G: Modulus of rigidity of the optical fiber Thus, in order to minimize the optical fiber's contribution to the torsional strength of the imaging core, the distance between the attachment points should be as far apart as possible. In practice, with the attachment points 124a and 124b as shown in FIG. 1A, the torque limiter 112 will fail after about 15° of windup and the optical fiber 124 will not fail until the optical connector 104 and tube 108 have turned several rotations.

By controlling the location of the fiber attachments in the current disclosure, the torque limiter 112 will break at a much smaller wind up than the optical fiber 124 will break. After the torque limiter 112 breaks, the optical fiber 124 takes up all the torque and will break at a lower torque than the torque limiter 112. In some embodiments, the native optical fiber 124 is weak enough that it does not need to be spliced and/or include its own break away joint.

In some embodiments, the optical fiber reduces axial strain on the torque limiter. However, axial stress and torsional stress on the torque limiter can be further decoupled by using helical cutouts in the torque limiter, as shown in FIGS. 4A and 4B. More specifically, the helical-shaped cutout 300 in the torque limiter 112 is configured such that the helical cut outs are in tension. This configuration reduces the risk of premature shearing of the torque limiter. In addition, if axial forces and torsional forces are encountered at the same time, the torque limiter will be deflected as shown in the computer simulation in FIG. 4B, but the torsional strength of the torque limiter will not be significantly reduced.

Figure 5:
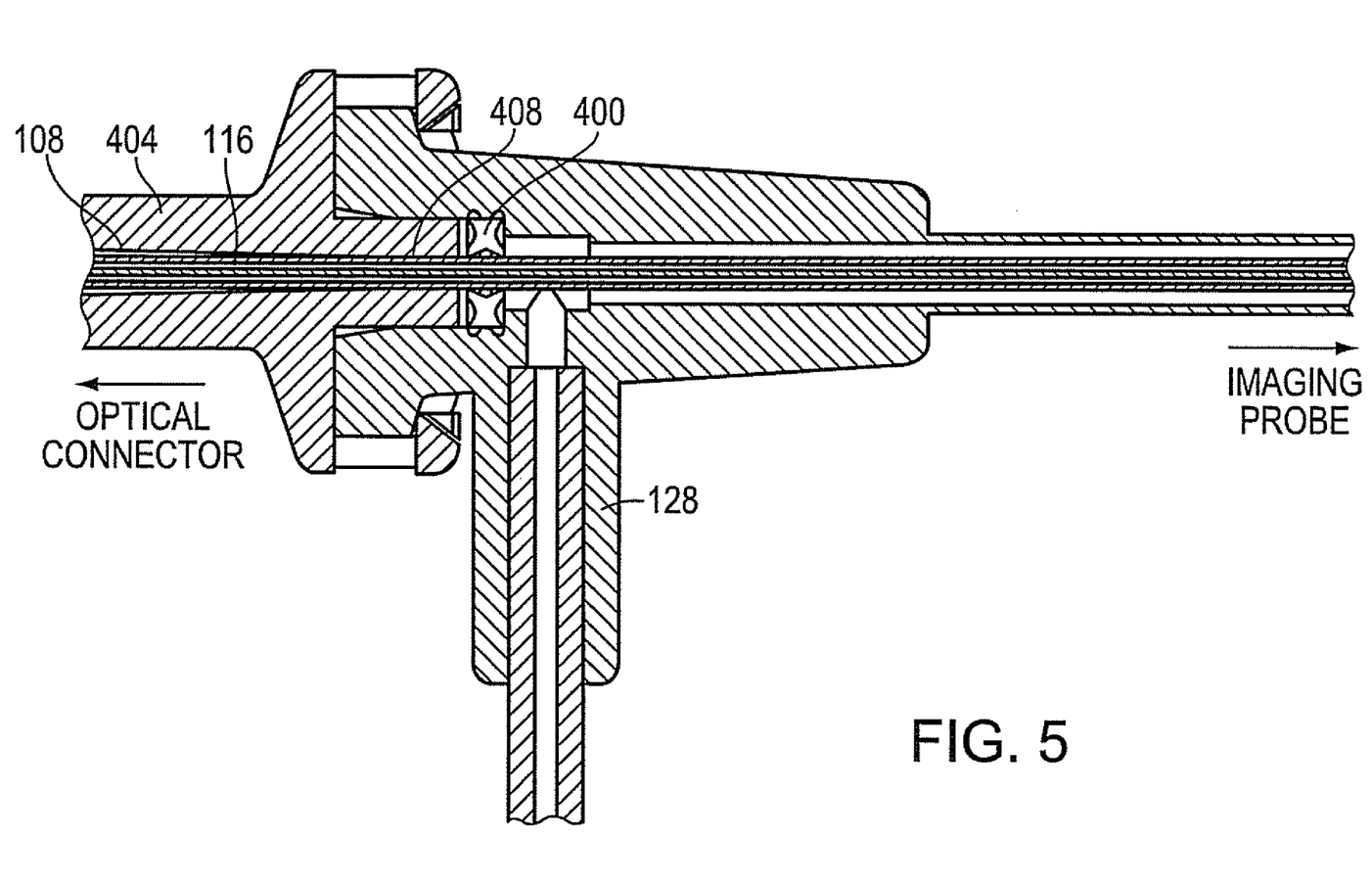
FIG. 5 is a schematic diagram showing a longitudinal cross-section of a rotating imaging system having a side port and seal, in accordance with an illustrative embodiment.

Referring back to FIG. 1B, in some embodiments, the system can include a side port 128 for accepting a fluid, such as a purge fluid. Purge fluid is injected through side port 128 to flush the catheter before imaging. Referring to FIG. 5, which shows a cross-sectional view of the side port 128, a seal 400 can be used to ensure that fluid does not travel proximally to the optical connector, but instead travels distally towards the optical probe. The seal 400 engages tube 108. In one embodiment, the seal 400 engages tube 108 at a location proximal to the torque limiter section. During imaging, the tube 108—which is in mechanical communication with the torque wire 116 and imaging probe—is rapidly pulled back towards the optical connector. Thus, seal 400 is designed to exclude fluid as the tube 108 slides and rotates through the seal aperture. In a preferred embodiment, the seal 400 is an elastomeric seal, such as a quad-ring, X-ring, or an O-ring. The seal 400 fits around tube 108 on the proximal side (relative to the optical connector) of the side port 128. To keep the tube 108 centered on the seal 400, the sheath 404 housing the seal 400 can have a necked down section 408 located close to the seal 400.

In the description, the invention is discussed in the context of optical coherency tomography imaging of a body lumen. However, those skilled in the art will appreciate that the invention can also be used in conjunction with other endoluminal devices and procedures (e.g., intravascular ultrasound) incorporating torque wires or other rotating components.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

What is claimed is:

1. An apparatus comprising:
(a) a first member defining a bore;
(b) a second member defining a bore, the first member and the second member being adjacent to one another, the bore of the first member being in concentric alignment with the bore of the second member;
(c) a torque wire disposed in the bore of the first member and in the bore of the second member; and
(d) a third member defining a bore, the second member and at least a portion of the first member being disposed in the bore of the third member, the third member being attached to the first member at a first attachment point of the third member, the third member being attached to the torque wire at a second attachment point of the third member, the second member disposed between the first attachment point and the second attachment point, the third member comprising at least one cutout between the first attachment point and the second attachment point; whereby rotational force imparted on the first member is transferred to the torque wire, and whereby the third member breaks and decouples the first member from the torque wire when the rotational force on the torque wire exceeds a predetermined amount.

2. The apparatus of claim 1, wherein the rotational force transferred to the torque wire is transferred from the third member having received the rotational force from the first member.

3. The apparatus of claim 1, wherein the first member comprises metal.

4. The apparatus of claim 3, wherein the metal comprises Nitinol.

5. The apparatus of claim 1, wherein the second member reduces flexure between the first attachment point and the second attachment point.

6. The apparatus of claim 1, wherein the third member comprises polyethylene terephthalate).

7. The apparatus of claim 6, wherein the polyethylene terephthalate) has a fracture strength of about 0.05 oz-in.

8. The apparatus of claim 1, wherein the torque wire defines an axial bore and the apparatus comprises an optical fiber disposed in the axial bore of the torque wire.

9. The apparatus of claim 8, wherein the optical fiber stretches in the axial direction less than about 0.005 inches.

10. An apparatus comprising:
  (a) a first member defining an axial bore;
  (b) a second member defining an axial bore in concentric alignment with the axial bore of the first member, the second member comprising a proximal end defining a first outer diameter and a distal end defining a second outer diameter, the second outer diameter being larger than the first outer diameter, the axial bore of the first member configured to concentrically receive the proximal end of the second member;
  (c) a torque wire disposed in the axial bore of the first member and the axial bore of second member; and
  (d) a third member defining an axial bore which concentrically receives at least a portion of the first member and the second member, the third member being attached to the first member at a first attachment point of the third member, the third member being attached to the torque wire at a second attachment point of the third member, the second member disposed between the first attachment point and the second attachment point, the third member comprising at least one cutout between the first attachment point and the second attachment point;

whereby rotational force imparted on the first member is transferred to the torque wire, and whereby the third member breaks and decouples the first member from the torque wire when the rotational force on the torque wire exceeds a predetermined amount.

11. The apparatus of claim 10, wherein the first member comprises metal.

12. The apparatus of claim 11, wherein the metal comprises Nitinol.

13. The apparatus of claim 10, wherein the second member reduces flexure between the first attachment point and the second attachment point.

14. The apparatus of claim 10, wherein the third member comprises poly(ethylene terephthalate).

15. The apparatus of claim 14, wherein the poly(ethylene terephthalate) has a fracture strength of about 0.05 oz-in.

16. The apparatus of claim 10, wherein the third member comprises two or more cutouts.

17. The apparatus of claim 10, wherein the torque wire defines an axial bore and the apparatus comprises an optical fiber disposed in the axial bore of the torque wire.

18. The apparatus of claim 17, wherein the optical fiber comprises glass fiber.

19. The apparatus of claim 17, wherein the optical fiber stretches in the axial direction less than about 0.005 inches.

20. The apparatus of claim 10, wherein the rotational force transferred to the torque wire is transferred from the third member having received the rotational force from the first member.

* * * * *